(12) United States Patent
Nagao

(10) Patent No.: US 8,503,746 B2
(45) Date of Patent: Aug. 6, 2013

(54) MEDICAL IMAGE PROCESSING DEVICE, MEDICAL IMAGE PROCESSING METHOD, AND MEDICAL IMAGE PROCESSING PROGRAM

(75) Inventor: Tomohiro Nagao, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 271 days.

(21) Appl. No.: 12/993,392

(22) PCT Filed: May 26, 2009

(86) PCT No.: PCT/JP2009/059575
§ 371 (c)(1),
(2), (4) Date: Nov. 18, 2010

(87) PCT Pub. No.: WO2009/145170
PCT Pub. Date: Dec. 3, 2009

(65) Prior Publication Data
US 2011/0069874 A1  Mar. 24, 2011

(30) Foreign Application Priority Data
May 26, 2008 (JP) .................................. 2008-136306

(51) Int. Cl.
*G06K 9/00* (2006.01)
(52) U.S. Cl.
USPC .......................................... 382/128; 382/191
(58) Field of Classification Search
USPC .................................................. 382/128, 154
See application file for complete search history.

(56) References Cited

U.S. PATENT DOCUMENTS

| 4,899,393 | A  | * | 2/1990  | Morishita et al. | ............. 382/130 |
| 5,570,404 | A  | * | 10/1996 | Liang et al.     | ............... 378/8 |
| 6,674,894 | B1 | * | 1/2004  | Parker et al.    | ............. 382/154 |
| 7,120,290 | B2 | * | 10/2006 | Parker et al.    | ............. 382/154 |
| 7,747,056 | B2 | * | 6/2010  | Suzuki et al.    | ............. 382/131 |
| 8,023,709 | B2 | * | 9/2011  | Joshi et al.     | ............. 382/130 |
| 8,126,227 | B2 | * | 2/2012  | Fujisawa         | ............. 382/128 |
| RE43,225  | E  | * | 3/2012  | Parker et al.    | ............. 382/154 |
| 8,311,308 | B2 | * | 11/2012 | Chen et al.      | ............. 382/131 |
| 8,345,944 | B2 | * | 1/2013  | Zhu et al.       | ............. 382/130 |
| 2004/0151355 | A1 | * | 8/2004 | Yokota et al.    | ............. 382/128 |
| 2008/0123800 | A1 | * | 5/2008 | Joshi et al.     | ............... 378/4 |
| 2008/0247619 | A1 | * | 10/2008 | Li              | ............. 382/128 |

FOREIGN PATENT DOCUMENTS

| JP | 2003-153894 | 5/2003 |
| JP | 2007-312892 | 12/2007 |

OTHER PUBLICATIONS

International Search Report in PCT/JP2009/059575.

* cited by examiner

*Primary Examiner* — Manav Seth
(74) *Attorney, Agent, or Firm* — Cooper & Dunham LLP

(57) ABSTRACT

A medical image processing device etc. which supports work for precisely identifying the area of a diagnosis object from a medical image scanned by a medical imaging apparatus is provided.
A CPU (11) of the medical image processing device (1) inputs image data and stores the same in a main memory (12) (S101). Next, the CPU (11) subjects the inputted image data to threshold processing (S102).
Next, the CPU (11) stores, in the main memory (12), data obtained by separating the area of the high signal values of the binarized image data into a bone region and an angiographically scanned region (S103).
Next, the CPU (11) identifies the contact area of the bone region and the angiographically scanned region from the data stored in the main memory (12) (S104).
Next, the CPU (11) emphasizes the contact area stored in the main memory (12) at the S104 and displays the contact area on a display device (15) (S105).

9 Claims, 7 Drawing Sheets

FIG.3
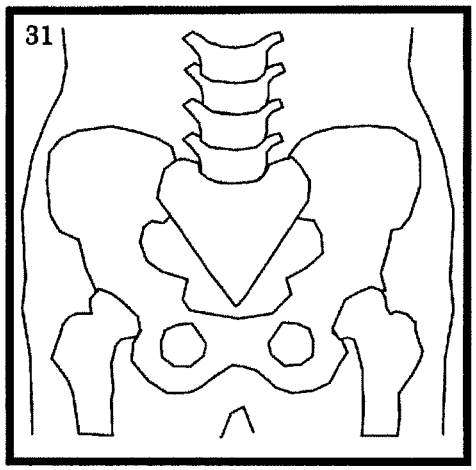
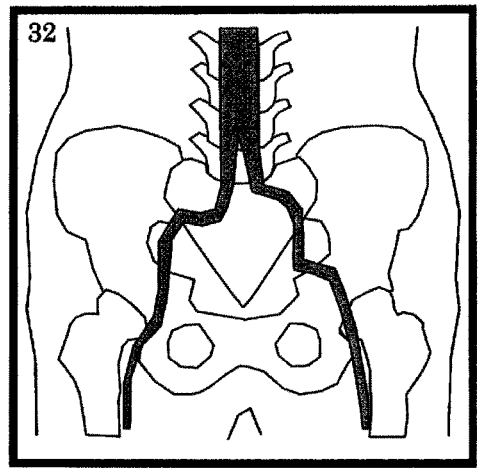
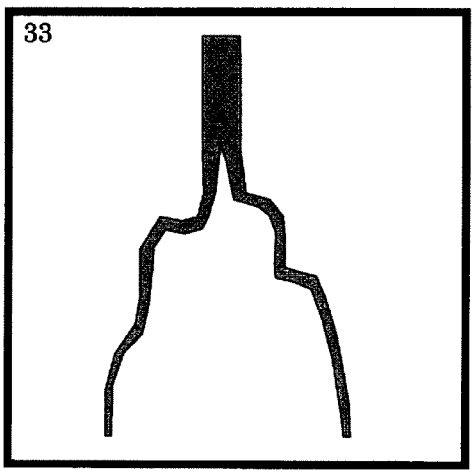
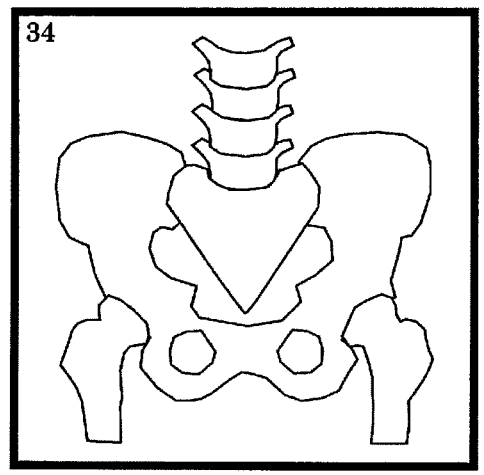
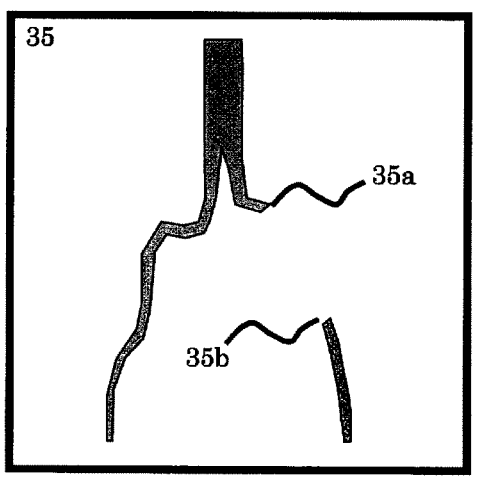
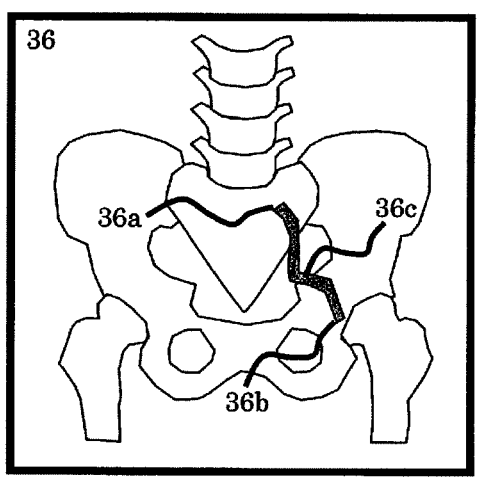

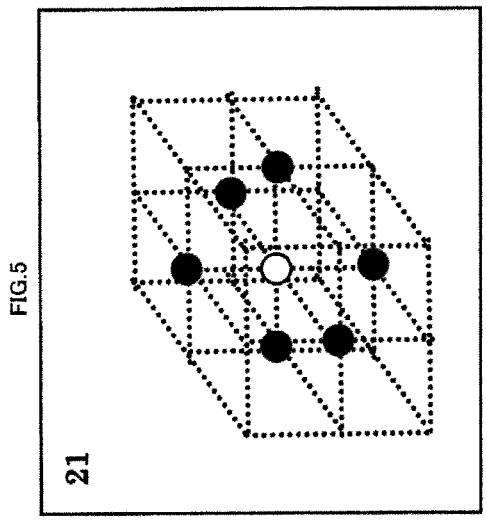
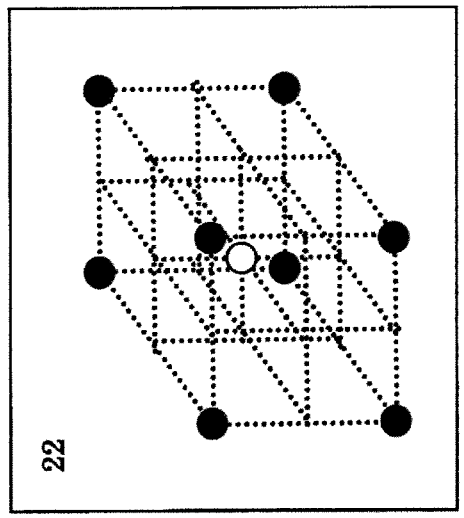
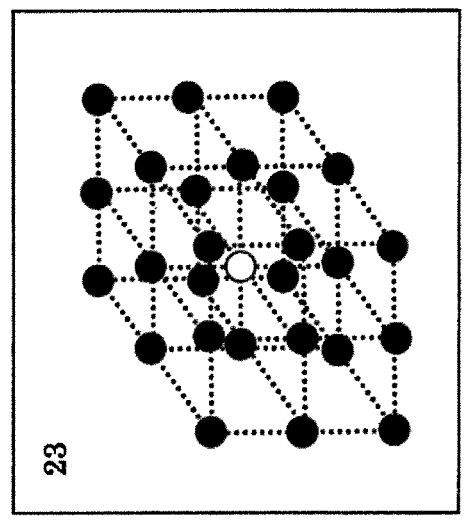
FIG.5

FIG.6
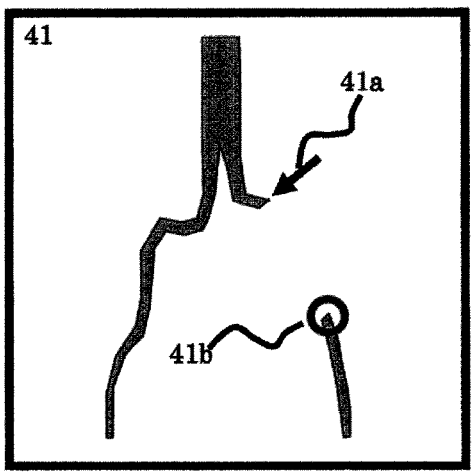
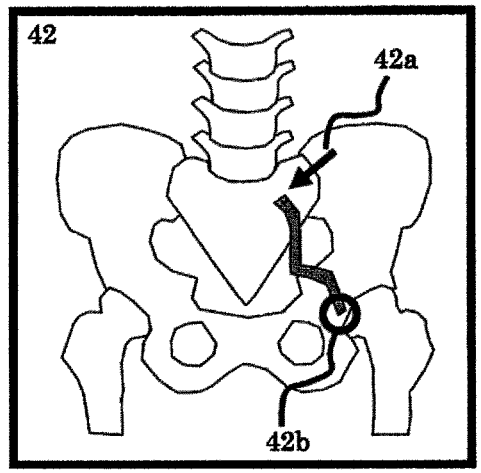
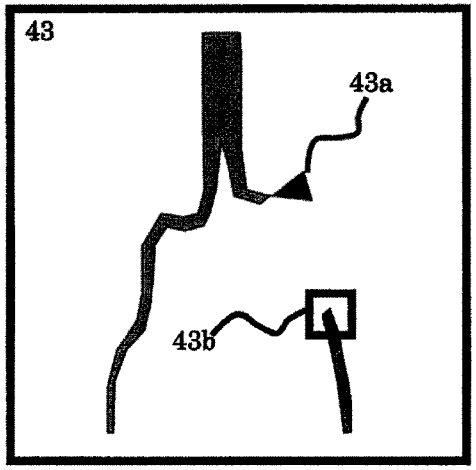
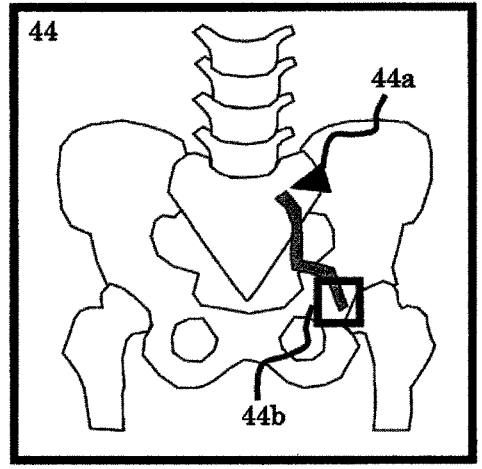
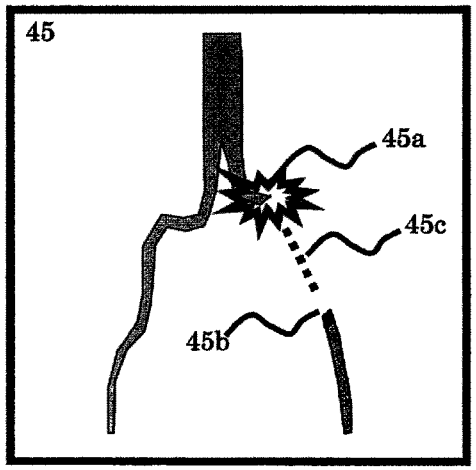
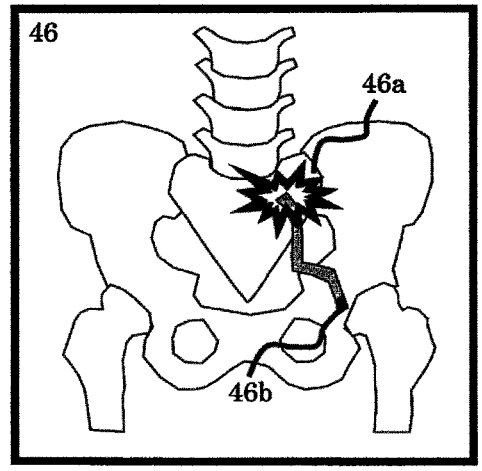

MEDICAL IMAGE PROCESSING DEVICE, MEDICAL IMAGE PROCESSING METHOD, AND MEDICAL IMAGE PROCESSING PROGRAM

FIELD OF THE INVENTION

The present invention relates to a medical image processing device etc. for executing image processing with respect to a medical image scanned by medical imaging apparatuses such as an X-ray CT apparatus and MRI apparatus.

DESCRIPTION OF RELATED ART

In recent years, due to improved performance of medical imaging apparatuses, a large number of high-resolution tomographic images can be scanned at one examination. And 3-dimensional image processing is performed based on such scanned tomographic images so as to implement diagnosis using 3-dimensional image data (includes image data generated from 3-dimensionally structured data of 2-dimensional image data). However, man-hour related to diagnosis performed by image-reading doctors is increasing inversely proportional to improvement in performance of medical image processing devices. Given this factor, demand for a technique to decrease man-hours related to diagnosis to be performed by image-reading doctors has increasing.

For example, even in angiography imaging for diagnosing a vascular disease such as aneurism, dissociation or stenosis, improvement in performance of medical imaging apparatuses enabled measurement of a whole body excluding a head region of an object to be examined in one imaging. Generally, in diagnosis of vascular disease using CT, images scanned by making the CT value of a blood vessel (to be precise, blood in a blood vessel) the same as one of bones using contrast agent are used. And currently, 3-dimensional image data reconstructed by the 3-dimensional image reconstruction method is being used besides diagnosis using axial images, in order to obtain morphological information of blood vessels more accurately. As for the 3-dimensional image reconstruction method, for example, the maximum intensity projection method (MIP) or volume rendering method is used.

As previously mentioned, since the CT value of a blood vessel imaged by using contrast medium (hereinafter referred to as "angiographically scanned region") becomes the same as the one of bones, a bone and an angiographically scanned region are extracted in approximately the same condition and displayed on a display device in the 3-dimensional reconstruction method. Meanwhile in the regions such as a head region, neck region and pelvic region, since a bone and a main blood vessel are adjoining to each other, the bone and the angiographically scanned region are extracted in approximately the same condition which makes it difficult to make a morphologic diagnosis of the blood vessel.

Given this factor, mainstream of current morphological diagnosis of blood vessels has been to reconstruct 3-dimensional images using the data after removing the bone region from original data (=image data scanned by a medical imaging apparatus). For the process to remove a bone region, the segmentation method such as the region removing process using ROI (Region of Interest), threshold value processing, or Region Growing method is to be used. A bone region is distinguished at once by these methods, and is removed from the original data. The conventional techniques related to the bone-removing process are disclosed in Patent Document 1 and Patent Document 2. There is another method using the mask processing which is included in the bone-removing process in a broad sense.

In the method disclosed in Patent Document 1, a bone region is distinguished and removed by obtaining the difference between the data of an image scanned without using contrast medium and the data of the image scanned using contrast medium, which requires two times of scanning for the same object. Since bones are rigid, if the body positions of the object are exactly the same, the bone region can be removed with high accuracy.

In the method disclosed in Patent Document 2, two kinds of threshold values A and B (A>B) are set with respect to the angiographically scanned region data, and the region that overlaps with threshold A from among the region extracted by the threshold value processing of threshold value B is removed as a bone region.

Patent Document 1: JP-A-2006-271527
Patent Document 2: JP-A-H11-318883

BRIEF SUMMARY OF THE INVENTION

The method disclosed in Patent Document 1 has a problem, since two times of scanning is required for the same object, that the he/she must be exposed to twofold greater radiation. Also, when the body positions of the object is changed between two times of scanning, accurate positioning is required between the image data without contrast agent and the image data with contrast agent.

The method disclosed in Patent Document 2 focuses only on luminance values, without considering the information related to structural configuration in a body such as bones or blood vessels. Therefore, in the case that there is a contrast-filled vessel region extracted by threshold A, the contrast-filled vessel region is removed. On the other hand, the bone region which is not extracted by threshold A remains as the contrast-filled vessel region without being removed. In this manner, the method disclosed in Patent Document 2 has a problem that contrast-filled vessel regions which should remain are removed, or the bone regions which should be removed remain in the data, depending on the values of thresholds A and B. These problems require a manual procedure to correct threshold values in order to execute accurate bone-removing process.

As described above, the conventional techniques including Patent Document 1 and Patent Document 2 require a great deal of labor from image-reading doctors for accurately executing the process to remove bone regions. This means that currently considerable amount of labor is required of image-reading doctors for accurately specifying a diagnostic region (for example, an angiographically scanned region) from a medical image.

The objective of the present invention, considering the above-described problems, is to provide a medical image processing device, medical image processing method and medical image processing program capable of supporting the process for accurately specifying a diagnostic region from a medical image which is scanned by a medical image apparatus.

A first invention for achieving the above-mentioned objective is a medical image processing device comprising:

a region extracting unit configured to extract a first region and a second region from a medical image;

a contact-area specifying unit configured to specify the contact area of the first region and the second region;

an image generating unit configured to generate an image in which the contact area and noncontact area are distinguished from each other; and a display unit configured to display the generated image.

The contact-area specifying unit in the first invention specifies the vicinity pixels of the first region as a contact area in the case that the vicinity pixels of the first region are included in the second region. Also, the contact-area specifying unit specifies the vicinity pixels of the first region as a contact area in the case that the vicinity pixels of the first region influenced by partial volume effect are included in the second region. Also, the contact-area specifying unit specifies the portion in which the first region and the second region are not clearly separated from each other as a contact area. Also, the contact-area specifying unit specifies the area in which the first region is discontinued as a contact area.

The first invention may further comprise a vicinity-pixel specifying unit configured to specify the number of vicinity pixels, wherein the contact-area specifying unit specifies a contact area based on the vicinity pixels of which the number is specified.

It is preferable that the image generating unit in the first invention generates a 3-dimensional image capable of distinguishing the contact area and the noncontact area from each other.

A second invention is a medical image processing method including:

a region extracting step that extracts a first region and a second region from a medical image;

a contact-area specifying step that specifies a contact area of the first region and the second region;

an image generating step that generates an image where the contact area and a noncontact area which is different from the contact area are distinguished from each other; and a displaying step that displays the generated image.

A third invention is a medical image processing program to cause a computer to execute:

a region extracting step that extracts a first region and a second region from a medical image;

a contact-area specifying step that specifies a contact area of the first region and the second region;

an image generating step that generates an image where the contact area and a noncontact area which is different from the contact area are distinguished from each other; and a displaying step that displays the generated image.

In accordance with the present invention, it is possible to provide a medical image processing device, etc. capable of supporting a process for accurately specifying a diagnostic region from a medical image scanned by a medical imaging apparatus.

BRIEF DESCRIPTION OF THE DIAGRAMS

FIG. 3 shows an example of image data to be used by medical image processing device 1.

FIG. 5 shows vicinity pixels.

FIG. 6 is a display example of a contact area.

DETAILED DESCRIPTION OF THE INVENTION

The preferable embodiments of the present invention will be described below in detail referring to the attached diagrams. The medical image processing device of the following embodiments will be described as the one for supporting a process for accurately specifying an angiographically scanned region from a medical image.

(1. Configuration of Medical Image Processing Device 1)

Figure 1:
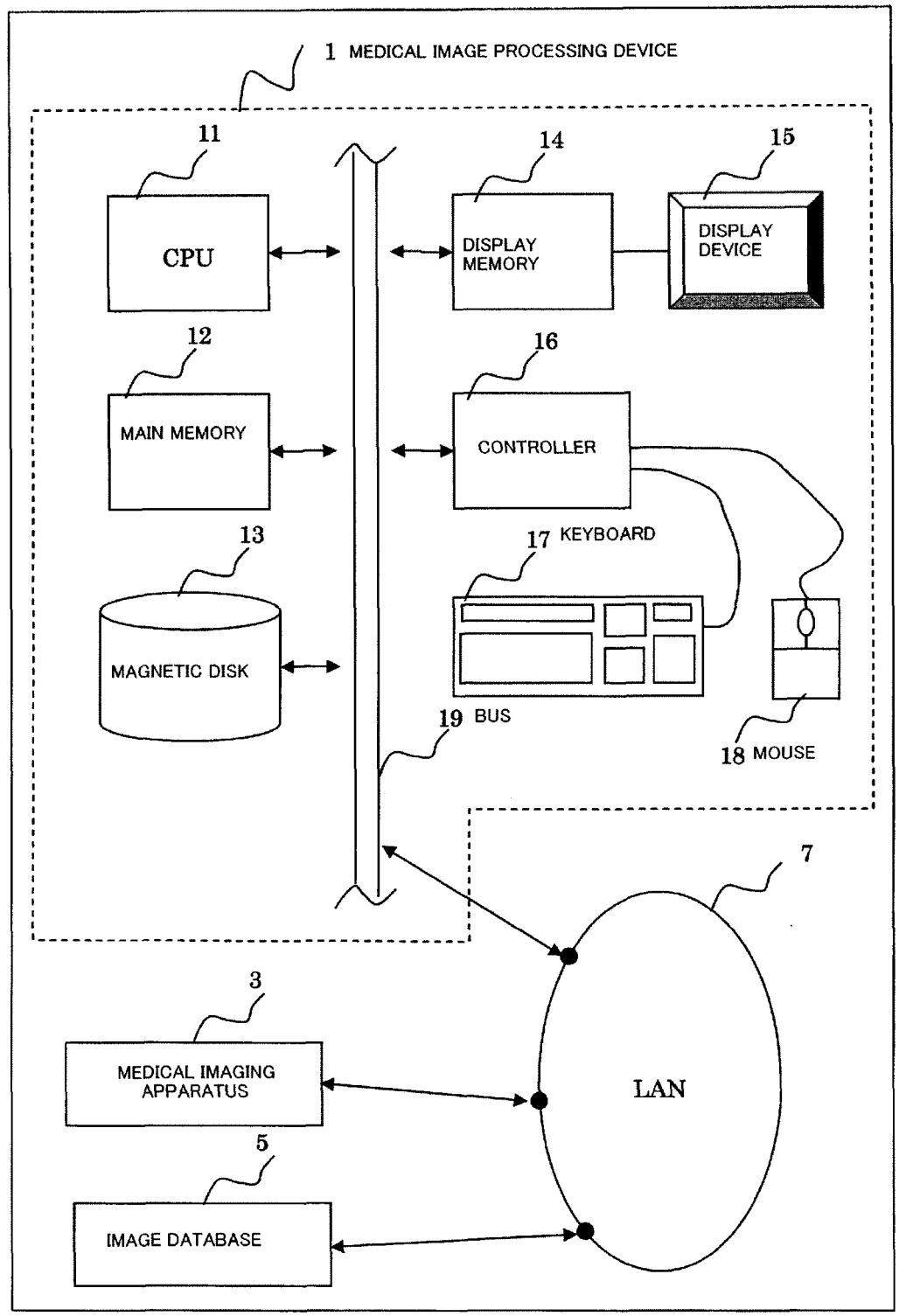
FIG. 1 is a hardware block diagram of medical image processing device 1.

First, configuration of medical image processing device 1 will be described referring to FIG. 1. FIG. 1 shows a hardware block diagram of medical image processing device 1. Medical image processing device 1 has a configuration that CPU 11, main memory 12, magnetic disk 13, display memory 14, display device 15 and controller 16 connected with keyboard 17 and mouse 18 are connected by bus 19. Medical image processing device 1 is connected to medical imaging apparatus 3 and image database 5 via LAN (Local Area Network) 7.

CPU 11 controls operation of the respective components. CPU 11 loads the data necessary for the program to be stored in magnetic disk 13 or for executing the program in main memory 12 and executes the program. Magnetic disk 13 stores medical images scanned by medical imaging apparatus 3. Magnetic disk 13 also stores the data necessary for the program to be executed by CPU 11 or for executing the program. Main memory 12 stores the program to be executed by CPU 11 or intermediate steps of calculation process.

Display memory 14 stores display data to be displayed on display device 15 such as a liquid crystal display or CRT. Keyboard 17 and mouse 18 are operation devices for an operator such as an image-reading doctor to give operation commands to medical imaging apparatus 1. Controller 16 detects condition of keyboard 17 and mouse 18, and outputs the detected condition to CPU 11 as signals.

Medical imaging apparatus 3 is for scanning medical images such as tomographic images of an object to be examined. Medical imaging apparatus 3 is, for example, an X-ray CT apparatus, MRI apparatus or ultrasonic imaging apparatus. Image database 5 is a database system for storing medical images scanned by medical imaging apparatus 3.

(2. Overall Operation of Medical Image Processing Device 1)

Figure 2:
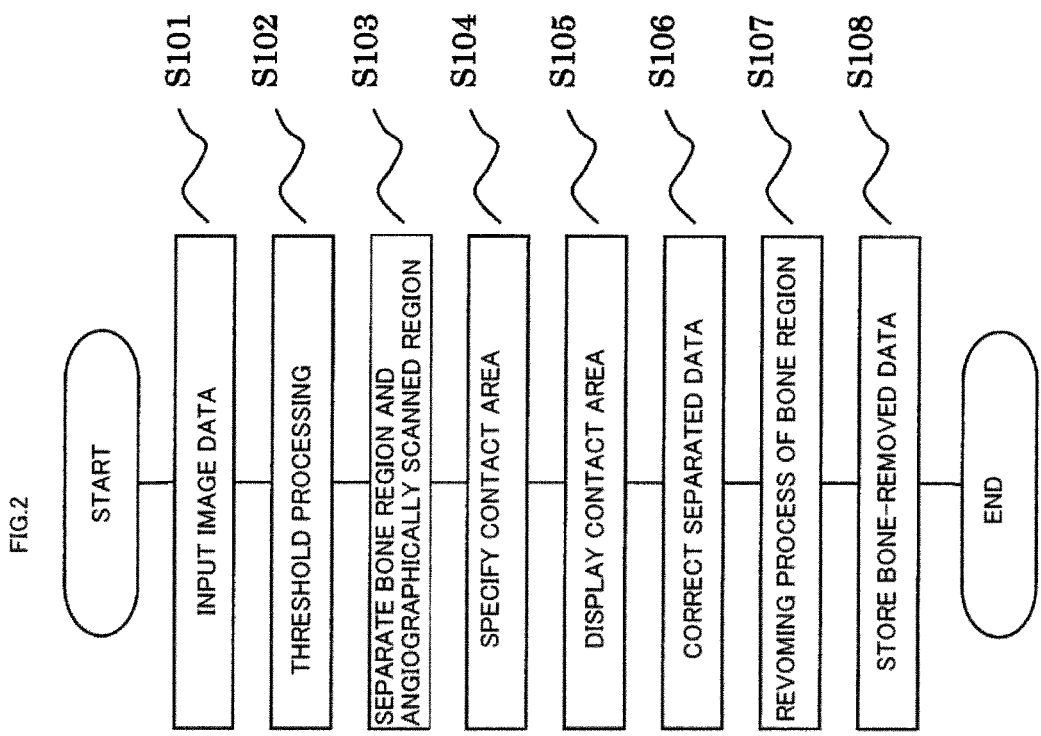
FIG. 2 is a flowchart showing an overall operation of medical image processing device 1.

Next, overall operation of medical image processing device 1 will be described referring to FIG. 2 and FIG. 3. FIG. 2 is a flowchart showing overall operation of medical image processing device 1. In the flowchart shown in FIG. 2, input data is the image scanned by an X-ray CT apparatus using contrast medium.

CPU 11 of medical image processing device 1 inputs image data and stores the inputted data in main memory 12 (S101). Image data is inputted from image database 5 via LAN 7. Inputted image data may be maintained in magnetic disk 13 and loaded in main memory 12.

Next, CPU 11 executes threshold processing with respect to the inputted image data (S102). In concrete terms, CPU 11 binarizes the inputted image data by the threshold value which can separate the region having high signal value including a bone region and an angiographically scanned region from the other region. For example, the value of the pixel included in the region having a high signal value is set as 1, and the value of the pixels included in the other region is set as 0. The threshold value to be used for the threshold value processing may be arbitrarily inputted by an operator, may be determined in advance, or may be automatically calculated by a statistical calculation method such as the clustering method for each inputted image data.

Next, CPU 11 stores the data wherein the region having a high signal value (pixel value 1) of the binarized image data is separated into a bone region and an angiographically scanned region to main memory 12 (S103). In S103, the bone region and the angiographically scanned region may be separated, for example, by the threshold value processing using a predetermined threshold value, etc. Also, the operator may specify a bone region and an angiographically scanned region via mouse 18 to separate them. The present invention supports the further accurate process for removing a bone region using the data in which a bone region and an angiographically scanned region are separated.

Next, CPU 11 specifies a contact area of a bone region and an angiographically scanned region from the data stored in main memory 12 in step S103 (S104). The details will be described later referring to FIG. 4.

Next, CPU 11 displays the contact area stored in main memory 12 in S104 on display unit 15 by distinguishing (for example, by enhancing) it from the region excluding the contact area (S105). Contact of a bone region and an angiographically scanned region may be caused due to biological reason or also by partial volume effect of CT. The operator visually identifies the contact area of the bone region and the angiographically scanned region displayed on display unit 15, and executes a process to remove the bone region which will be described later.

Next, the operator specifies the region where a bone region and an angiographically scanned region are mixed using mouse 18 in order to properly correct the mixed region displayed on display unit 15. The CPU 11 corrects the data of the specified region (S106).

Next, CPU 11 removes the bone region corrected in S106 from the image data inputted in S101, or sets the bone region as mask data. That is, CPU 11 executes the process to remove a bone region with respect to the data corrected in S106 (S107).

Next, CPU 11 stores the data from which the bone region is removed as bone-removed data in magnetic disk 13 (S108).

FIG. 3 shows an example of image data to be used by medical image processing device 1. Image data 31 is data of the image scanned without contrast medium. Image data 32 is data of the image scanned with contrast medium. Image data 33 shows the difference between image 32 and image data 31 obtained by positioning image data 31 with respect to image data 32. Such generated image 33 shows an angiographically scanned region. Image data 34 shows the data wherein the threshold value processing for extracting the region having a high signal value is executed on image data 31. Such generated image data 34 shows a bone region.

Also, image data 33 indicating an angiographically scanned and image data 34 indicating a bone region can be generated by another method. First, the threshold value processing for extracting the high signal value region including an angiographically scanned region and a bone region is executed on image data 32. Then the bone region and the angiographically scanned region are separated by the threshold value processing. Or, the operator specifies the bone region and the angiographically scanned region via mouse 18, etc. and separates them. In this case, image data 31 is not necessary, and only one time of imaging is required.

When a bone region and an angiographically scanned region are clearly separated such as image data 33 and image data 34, the process for removing the bone region is completed. That is, CPU 11 of medical image processing device 1 maintains image data 33 in magnetic disk 13 as bone-removed data. On the other hand, in the case that a bone region and an angiographically scanned region are not clearly separated and the image such as image data 33 and image data 34 can not be obtained, the process for removing a bone region is to be continued.

Image data 35 is an example of the case that a bone region and an angiographically scanned region are not clearly separated after being generated by the same process as performed on image data 33. Image data 36 is an example of the case that a bone region and an angiographically scanned region are not clearly separated after being generated by the same process as performed on image data 34. In image data 35, there is a portion where the angiographically scanned region is discontinued. On the other hand, image data 36 includes a part of the angiographically scanned region in addition to the bone region.

For example, in the case that the 3-dimensional image constructed by the maximum value projection method based on the separation result of image data 35 and image 36 is displayed on display device 15, there is a good possibility that the operator cannot identify the angiographically scanned region which is mixed and included in a bone region. Given this factor, in the present invention, end portions 35a and 35b of the discontinued angiographically scanned regions in image data 35 are enhanced and displayed. In this manner, it is easy for the operator to find the discontinued portions. Also, in the present invention, end portions 36a and 36b of angiographically scanned region 36c included in image data 36 are enhanced and displayed. By doing so, it makes it easier for the operator to find the angiographically scanned region mixed within a bone region.

(3. Process to Specify a Contact Area)

Figure 4:
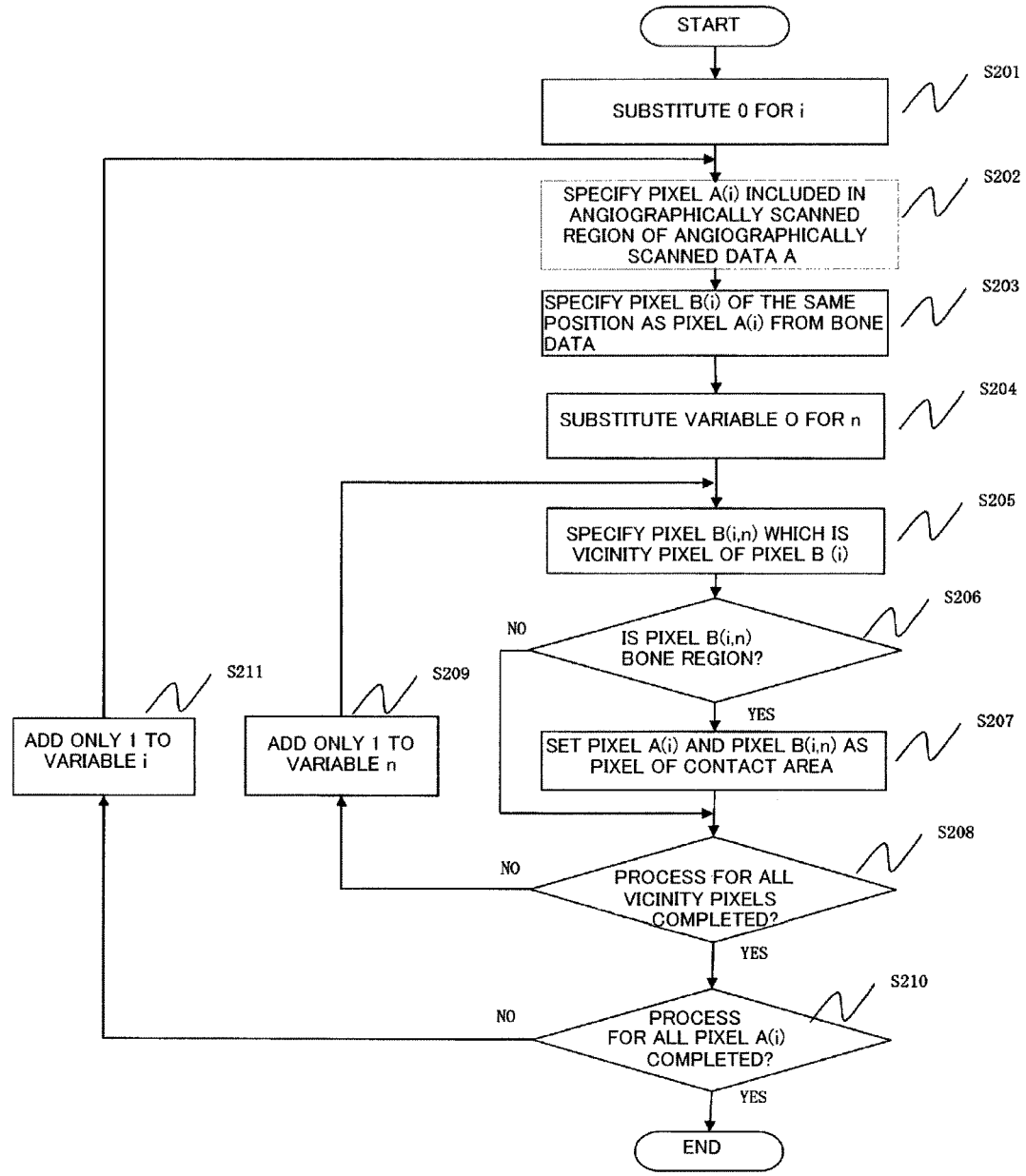
FIG. 4 is a flowchart showing a process for specifying a contact area.

Next, a process for specifying a contact area will be described referring to FIG. 4 and FIG. 5. FIG. 4 is a flowchart showing a specifying process of a contact area. In FIG. 4, the process is executed by medical image processing device 1 and angiogrpahically scanned region data A (image data 35 in FIG. 3) and bone data B (image data 36 in FIG. 3) are loaded in main memory 12.

CPU 11 substitutes 0 with variable i which is loaded in main memory 12. Variable i is a number for specifying the pixel included in the angiographically scanned region of angiographically scanned region data A loaded in main memory 12. There are pixels in angiographically scanned region data A that are not included in an angiographically scanned region. Thus, for example, a number is to be appended only on the pixel included in the angiographically scanned region.

Next, CPU 11 specifies pixel A(i) included in an angiographically scanned region of angiographically scanned region data A (S202). Then CPU 11 specifies pixel B(i) which is at the same position as pixel A(i) from bone data B loaded in main memory 12 (S203). There are pixels in bone data B that are not included in a bone region. Thus, for example, a flag for indicating whether it is the pixel included in the bone region or not is to be appended on each pixel of bone data B.

Next, CPU 11 substitutes 0 with variable n which is loaded in main memory 12 (S204). Here, variable n is a pixel included in bone data B, and is a number to specify the vicinity pixel of pixel B(i). Then CPU 11 specifies pixel B(i,n) which is a vicinity pixel of pixel B(i) (S205). Vicinity pixels will be described later in explanation of FIG. 5.

Next, CPU 11 confirms whether pixel B(i,n) is included in a bone region or not (S206). When pixel B(i,n) is included in the bone region (YES in S206), CPU 11 sets a flag on pixel A(i) and pixel B(i,n) indicating it as the pixel of a contact region (S207). In other words, pixel A(i) indicates itself as a contact region in angiographically scanned region data A. Also, pixel B(i,n) indicates itself as a contact region in bone data B. When pixel B(i,n) is not included in the bone region (No of S206), CPU 11 proceeds to S208.

Next, CPU 11 confirms whether the process is completed in all of the vicinity pixels or not (S208). When the process is not completed in all of the vicinity pixels (No in S208), CPU 11 adds only 1 to variable n (S209), and repeats the process from S205. On the other hand, when the process is completed in all of the vicinity pixels (YES in S208), CPU 11 proceeds to S210.

Next, CPU 11 confirms whether the process is completed for all of pixel A(i) included in the angiographically scanned region of angiographically scanned region data A or not (S210). When the process is not completed in all of pixel A(i) (NO in S210), CPU 11 adds only 1 to variable i (S211), and repeats the process from S202. On the other hand, when the process is completed in all of pixel A(i) (YES in S210), CPU 11 ends the process.

FIG. 5 is for explaining vicinity pixels. Volume data 21 is an example in the case that the number of vicinity pixels is defined as 6. A white circle or a black circle indicates the center point of a pixel. The white circle is the center point of a processing target pixel. The black circle is the center point of a vicinity pixel. Also, volume data 22 is an example in the case that the number of pixels is defined as 8. Volume data 23 is an example in the case that the number of pixels is defined as 26. The number and the position, etc. can be arbitrarily set via keyboard 17 or mouse 18. As shown in FIG. 5, by setting the pixel adjacent in every direction viewing from the processing target pixel as a vicinity pixel, it is possible to specify the pixel as a contact region even if it looks as if the region where a blood vessel and a bone are not in contact from a certain viewpoint and also looks as the region where the blood vessel and the bone are in contact from another viewpoint.

(4. Display Process of a Contact Region)

Next, a process for displaying a contact area will be described referring to FIG. 6. FIG. 6 is an example for displaying a contact area. Image data 41, 43 and 45 are enhanced display of the contact area shown in image data 35 of FIG. 3. mIage data 42, 44 and 46 are enhanced display of the contact area in image data 36 of FIG. 3.

In image data 41 and 42, the end portions of a contact area are indicated by arrows 41a and 42a. Also, in image data 41 and 42, the end portions of a contact area are shown by circles 41b and 42b.

In image data 43 and 44, the end portions of a contact area are indicated by triangles 43a and 44a. Also, in image data 43 and 44, the end portions of a contact area are indicated by squares 43b and 44b.

In image data 45 and 46, the end portions of a contact area are indicated by light-emitting or blinking displays 45a and 46a. Also, in image data 45 and 46, end portions of a contact area are indicated by color displays 45b and 46b. In this manner, by enhanced display of the end portions of a contact area, the end portions of a contact area can be pointed out to the operator.

In addition, it is preferable that the pattern of enhanced display (arrows, circles, triangles, squares, light-emitting or blinking, or coloring) is arbitrarily variable. Also as shown in FIG. 6, it is desirable that the same enhanced display of a contact area is used (for example, arrow 42a) in bone data (for example, image data 42) as the enhanced display of a contact area (for example, arrow 41a) in angiographically scanned region data (for example, image data 41) by corresponding to each other. This makes it easier for the operator to recognize their corresponding relationship. Further, as for the discontinued angiograhically scanned portion in angiographically scanned region data (for example, image data 45), it is desirable to display it with a virtual line having a different color, thickness or shape from surrounding angiographically scanned regions (for example, dotted line 45c). In this manner, the operator can easily distinguish the blood vessel which is difficult to identify in bone data (for example, image data 46).

(5. Process for Displaying Plural Reconstructed Images)

Figure 7:
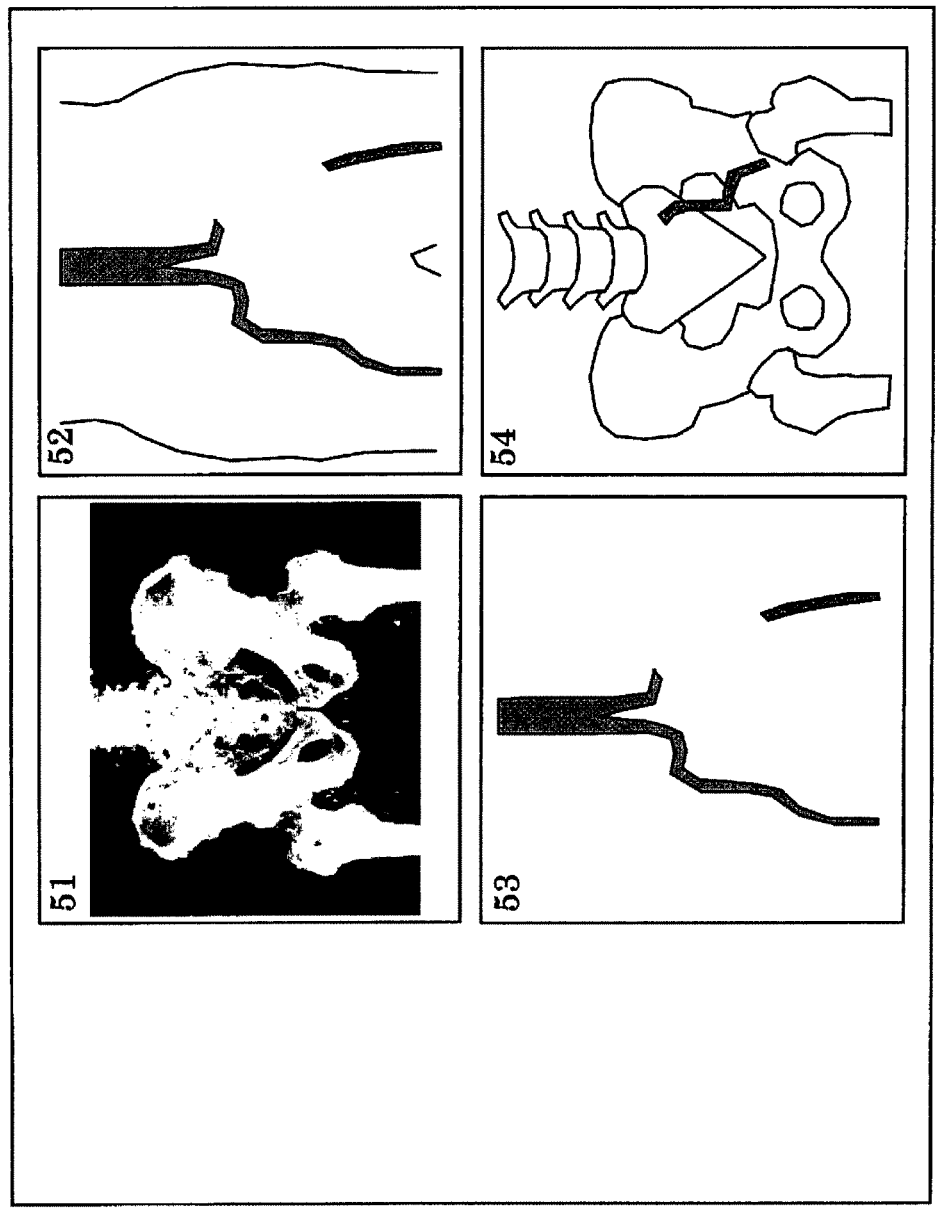
FIG. 7 is a display example of a plurality of reconstructed images.

Next, a process for displaying a plurality of reconstructed images will be described referring to FIG. 7. FIG. 7 is a display example of a plurality of reconstructed images. Image data 51 is original data acquired from image database 5. Image data 52 is bone-removed data. Image data 53 is angiographically scanned region data. Image data 54 is bone data.

In a display region of image data 51, a tomographic image such as axial, coronal, sagittal or MPR (Multi Planar Reformation), or a 3-dimensional image constructed by the MIP method or volume rendering method are to be displayed. Also in the display region of image data 52, it is desirable to display the result of sequential differences between image data 51 of original data and image 54 of bone data using the MIP method, etc. In this manner, the operator can sequentially confirm the result of the bone-removing process executed in a bone region. Also in image data 53, it is desirable to display image data 51 of original data by overlapping with an angiographically scanned region. In the same manner, it is desirable to display image data 51 of original data by overlapping with a bone region. Then in the display region of image data 52 and 53, the contact area of an angiographically scanned region and a bone region is to be enhanced for display. Enhanced display of a contact area in a 3-dimensional image is effective for, for example, 3-dimensional correction such as clipping using ROI.

As for another display pattern, any of angiographically scanned region data, bone data or bone-removed data (a tomographic image by MPR or a 3-dimensional image by the method such as MIP method or volume rendering method) can be displayed by switching them in one screen (a first screen). Then in the three remaining screens, the angiographically scanned region data, bone data or bone-removed data displayed on the first screen can be overlapped with the three tomographic images of axial, coronal and sagittal image.

As mentioned above, in accordance with the embodiment of the present invention, medical image processing device 1 extracts a first region and a second region from a medical image scanned by medical imaging apparatus 3, specifies a contact area of the extracted first region and the second region, and displays a medical image on display device 15 by enhancing the specified contact area. For example, the first region is an angiographically scanned region and the second region is the bone region. Also, the first region may be a bone region and the second region may be a contras-filled blood vessel region. Also by setting the first region as an angiographically scanned region and the second region as a fat region, they can be applied for the process to remove a fat region.

In accordance with the embodiment of the present invention, it is possible to visually and easily identify a blood vessel which can be easily removed by mistake or a bone which can easily fail to be removed from the image scanned by a medical imaging apparatus such as an X-ray CT apparatus, which leads to a support for accurately removing a bone region. Also, while display condition of a contact area is described as "enhanced display", it may be displayed by qualifying the area i.e. darkening a contact area, etc. as long as the contact area is distinguishable.

The preferable embodiments of the medical image processing device, etc. according to the present invention have been described. However, the present invention is not limited to these embodiments. It is obvious that persons skilled in the art can make various kinds of alterations or modifications within the scope of the technical idea disclosed in this application, and it is understandable that they belong to the technical scope of the present invention.

DESCRIPTION OF REFERENCE NUMERALS

1: medical image processing device, 3: medical imaging apparatus, 5: image database, 7: LAN, 11: CPU, 12: main memory, 13: magnetic disk, 14: display memory, 15: display device, 16: controller, 17: keyboard, 18: mouse, 19: bus, 21~23: volume data, 31~36, 41~46 and 51~54: image data

The invention claimed is:

1. A medical image processing device comprising:
a region extracting unit configured to extract a first region and a second region from a medical image;
a contact-area specifying unit configured to specify at least one pixel of the second region which is a vicinity pixel of the first region as a contact area of the first region and the second region;
an image generating unit configured to generate an image in which the contact area and a noncontact area that is different from the contact area are distinguished; and
a display unit configured to display the generated image.

2. The medical image processing device according to claim 1, wherein the first region is one of an angiographically scanned region and a bone region and the second region is another of the angiographically scanned region and the bone region.

3. The medical image processing device according to claim 1, wherein the contact area specifying unit specifies the vicinity pixel of the first region as a contact area when the vicinity pixel of the first region influenced by partial volume effect of CT is included in the second region.

4. The medical image processing device according to claim 1, wherein the contact area specifying unit specifies the portion where the first region and the second region are not separated as a contact area.

5. The medical image processing device according to claim 1, wherein the contact area specifying unit specifies the portion where the first region is discontinued as a contact area.

6. The medical image processing device according to claim 2 comprising a vicinity pixel specifying unit configured to specify the number of the vicinity pixels, wherein the contact area specifying unit specifies a contact area based on the vicinity pixels of which the number is specified.

7. The medical image processing device according to claim 1, wherein the image generating unit generates a 3-dimensional image in which the contact area and the noncontact area that is different from the contact area are distinguished from each other.

8. A medical image processing method, performed by a medical image processing device, the medical image processing method comprising:
a region extracting step that extracts a first region and a second region from a medical image;
a contact-area specifying step, performed by the medical image processing device, to specify at least one pixel of the second region which is a vicinity pixel of the first region as a contact area of the first region and the second region;
an image generating step that generates an image in which the contact area and a noncontact area that is different from the contact area are distinguished from each other; and
a displaying step that displays the generated image.

9. A medical image processing program including computer executable instructions embodied in a non-transitory computer-readable medium, and when executed, cause a computer to perform a method comprising:
a region extracting step that extracts a first region and a second region from a medical image;
a contact area specifying step that specifies a contact-area specifying unit configured to specify at least one pixel of the second region which is a vicinity pixel of the first region as a contact area of the first region and the second region;
an image generating step that generates an image in which the contact area and a noncontact area that is different from the contact area are distinguished from each other; and
a displaying step that displays the generated image.

* * * * *